(12) United States Patent
Cheng et al.

(10) Patent No.: US 7,442,721 B2
(45) Date of Patent: Oct. 28, 2008

(54) DURABLE BIOCOMPATIBLE CONTROLLED DRUG RELEASE POLYMERIC COATINGS FOR MEDICAL DEVICES

(75) Inventors: Peiwen Cheng, Santa Rosa, CA (US); Mingfei Chen, Santa Rosa, CA (US); Kishore Udipi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 287 days.

(21) Appl. No.: 11/279,762

(22) Filed: Apr. 14, 2006

(65) Prior Publication Data

US 2007/0244284 A1  Oct. 18, 2007

(51) Int. Cl.
  *A61K 47/32* (2006.01)
(52) U.S. Cl. ............... 514/772.4; 514/772.6; 524/558; 526/318.41; 526/320

(58) Field of Classification Search ................ 524/558; 526/318.41, 320; 514/772.4, 772.6
See application file for complete search history.

(56) References Cited

U.S. PATENT DOCUMENTS

| 6,143,322 A | * | 11/2000 | Sackler et al. | ............... 424/459 |
| 6,286,955 B1 | * | 9/2001 | Akashi | ............... 351/160 H |
| 6,530,950 B1 | | 3/2003 | Alvarado et al. | |
| 6,653,426 B2 | | 11/2003 | Alvarado et al. | |

FOREIGN PATENT DOCUMENTS

JP  50024588 A  *  3/1975

* cited by examiner

*Primary Examiner*—Bernard Lipman

(57) ABSTRACT

Disclosed herein are biocompatible durable controlled drug releasing polymeric coatings for medical devices. The drug release rates of the polymers are controlled by adjusting monomer ratios and glass transition temperatures Tgs. The polymers are durable; they do not delaminate from the coated medical device.

14 Claims, 3 Drawing Sheets

DURABLE BIOCOMPATIBLE CONTROLLED DRUG RELEASE POLYMERIC COATINGS FOR MEDICAL DEVICES

FIELD OF THE INVENTION

The invention disclosed herein relates to durable controlled drug eluting polymeric coatings for implantable medical devices.

BACKGROUND OF THE INVENTION

Medical devices are used for myriad purposes on and throughout a human body. They can be simple ex vivo devices such as adhesive bandages, canes, walkers and contact lenses or complex implantable devices including pacemakers, heart valves, vascular stents, catheters and vascular grafts. Implantable medical devices must be biocompatible to prevent inducing life threatening adverse physiological responses between the implant recipient and device.

Recently, highly biocompatible polymers have been formulated to provide implantable medical devices with coatings. These coatings not only increase an implant's tissue compatibility but can also function as bioactive agent reservoirs. However, designing polymer coatings for medical devices has proven problematic. All medical device coatings must be non-toxic, durable and adhere well to device surfaces. Additionally, when the medical device comes into intimate contact with unprotected tissues such as blood and internal organs it must also be biocompatible. Furthermore, if the medical device is designed to be pliable either in operation or deployment, the coating must resist cracking, fracture and delamination.

Moreover, medical devices intended to act as bioactive agent (drug) reservoirs must not only be biocompatible, structurally stable and resistant to delamination, but also chemically compatible with the drug to be deployed. Furthermore, if the reservoir is also intended to control the drug's release rate into adjacent tissue the polymer used must possess other highly specialized properties as well.

Moreover, medical devices intended to act as bioactive agent (drug) reservoirs must not only be biocompatible, structurally stable and resistant to delamination, but also chemically compatible with the drug to be deployed. Furthermore, if the reservoir is also intended to control the drug's release rate into adjacent tissue the polymer used must possess other highly specialized properties as well.

Drug-polymer physical chemistry and the physical characteristics of the coating itself, such as coating thickness, are the two most important factors in determining a polymer matrix's drug elution profile. Highly compatible drug-polymer combinations usually result in more even elution rates and are therefore preferable for most in vivo applications. Polymer-drug compatibility is a function of drug-polymer miscibility. The degree of miscibility, or compatibility, between a drug and a polymer carrier can be ascertained by comparing their relative solubility parameters. However, as will be more fully developed below, balancing drug elution rates with biocompatibility, ductility and adhesiveness requires more than merely matching a single polymer with a drug based on their total solubility parameters alone.

Cardiovascular disease, specifically atherosclerosis, remains a leading cause of death in developed countries. Atherosclerosis is a multifactorial disease that results in a narrowing, or stenosis, of a vessel lumen. Briefly, pathologic inflammatory responses resulting from vascular endothelium injury causes monocytes and vascular smooth muscle cells (VSMCs) to migrate from the sub endothelium and into the arterial wall's intimal layer. There the VSMC proliferate and lay down an extracellular matrix causing vascular wall thickening and reduced vessel patency.

Cardiovascular disease caused by stenotic coronary arteries is commonly treated using either coronary artery by-pass graft (CABG) surgery or angioplasty. Angioplasty is a percutaneous procedure wherein a balloon catheter is inserted into the coronary artery and advanced until the vascular stenosis site is reached. The balloon is then inflated restoring arterial patency. One angioplasty variation includes arterial stent deployment. Briefly, after arterial patency has been restored, the balloon is deflated and a vascular stent is deployed into the vessel lumen at the stenosis site. The catheter is then removed from the coronary artery and the deployed stent remains implanted to prevent the newly opened artery from constricting spontaneously. However, balloon catheterization and stent deployment can result in vascular injury ultimately leading to VSMC proliferation and neointimal formation within the previously opened artery. This biological process whereby a previously opened artery becomes re-occluded is referred to as restenosis.

The introduction of intracoronary stents into clinical practice has dramatically changed treatment of obstructive coronary artery disease. Since having been shown to significantly reduce restenosis as compared to percutaneous transluminal coronary angioplasty (PTCA) in selected lesions, the indication for stent implantation was been widened substantially. As a result of a dramatic increase in implantation numbers worldwide in less selected and more complex lesions, in-stent restenosis (ISR) has been identified as a new medical problem with significant clinical and socioeconomic implications. The number of ISR cases is growing: from 100,000 patients treated worldwide in 1997 to an estimated 150,000 cases in 2001 in the United States alone. ISR is due to a vascular response to injury, and this response begins with endothelial denudation and culminates in vascular remodeling after a significant phase of smooth muscle cell proliferation.

At least four distinct phases of reaction can be observed in ISR: thrombosis, inflammation, proliferation, and vessel remodeling. There is a wide spectrum of conventional catheter-based techniques for treatment of ISR, ranging from plain balloon angioplasty to various atherectomy devices and repeat stenting. One possible method for preventing restenosis is the administration of anti-inflammatory compounds that block local invasion/activation of monocytes thus preventing the secretion of growth factors that may trigger VSMC proliferation and migration. Other potentially anti-restenotic compounds include anti-proliferative agents such as chemotherapeutics including rapamycin and paclitaxel. However, anti-inflammatory and anti-proliferative compounds can be toxic when administered systemically in anti-restenotic-effective amounts. Furthermore, the exact cellular functions that must be inhibited and the duration of inhibition needed to achieve prolonged vascular patency (greater than six months) is not presently known. Moreover, it is believed that each drug may require its own treatment duration and delivery rate. Therefore, in situ, or site-specific drug delivery using anti-restenotic coated stents has become the focus of intense clinical investigation. Once the coated stent is deployed, it releases the anti-restenotic agent directly into the tissue thus allowing for clinically effective drug concentrations to be achieved locally without subjecting the recipient to side effects associated with systemic drug delivery. Moreover, localized delivery of anti-proliferative drugs directly at the treatment site eliminates the need for specific cell targeting technologies.

Human clinical studies on stent-based anti-restenotic delivery have demonstrated excellent short-term anti-restenotic effectiveness. However, side effects including vascular erosion have also been seen. Vascular erosion can lead to stent instability and further vascular injury. Furthermore, the extent of cellular inhibition may be so extensive that normal re-endothelialization will not occur. The endothelial lining is essential for maintaining vascular elasticity and as an endogenous source of nitric oxide. Therefore, compounds that exert localized anti-restenotic effects while minimizing vascular and cellular damage are essential for the long-term success of drug delivery stents.

SUMMARY OF THE INVENTION

The present invention relates to durable biocompatible controlled drug release polymers for coating and forming implantable medical devices. The polymers of the present invention form drug encapsulating matrices that enable controlled release of drugs. More specifically the drug release, or eluting, rates are controlled by, amongst other properties, the glass transition temperature (Tg) of the polymer. The biocompatible controlled-release coatings described herein are durable, that is they do not delaminate from the medical device or suffer damage rendering the coating inoperable. The polymers of the present invention are biocompatible and stable, that is they do not biodegrade. Additionally, the polymers of the present invention are stable to ethylene oxide sterilization.

Medical devices suitable for coating with the durable controlled drug releasing polymers of the present invention include, but are not limited to, vascular stents, stent grafts, urethral stents, bile duct stents, catheters, guide wires, pacemaker leads, bone screws, sutures and prosthetic heart valves. Medical devices which can be manufactured from the durable controlled drug releasing polymers of the present invention include, but are not limited to, vascular stents, stent grafts, urethral stents, bile duct stents, catheters, guide wires, pacemaker leads, bone screws, sutures and prosthetic heart valves.

The durable biocompatible controlled drug releasing polymers comprise a single monomer, or two or more monomers. In one embodiment of the present invention, the durable controlled drug releasing polymers comprise acrylic monomers. Additional monomers useful in the polymers include, but are not limited to, polyethylene glycol acrylate esters. By varying the amount ratio of monomers used as well the reaction conditions the properties of the polymers can be fine tuned for drug delivery, more specifically controlled drug release rates. The polymers of the present invention are also suitable for the controlled-release of both hydrophobic and hydrophilic drugs, either independently or in combination.

In one embodiment of the present invention, a durable controlled drug releasing polymeric coating is provided for an implantable medical device comprising one or more monomers selected from the group consisting of 2-ethoxyethyl methacrylate and acrylate monomers. In another embodiment, the acrylate monomers are selected from the group consisting of hexyl methacrylate, butyl methacrylate, ethyl methacrylate, lauryl methacrylate, hydroxyl propylmethacrylate and hydroxyl ethylmethacrylate.

In another embodiment of the present invention, a durable controlled drug releasing polymeric coating is provided for an implantable medical device wherein the one or more monomers is 2-ethyoxyethyl methacrylate.

In yet another embodiment of the present invention, a durable controlled drug releasing polymeric coating is provided for an implantable medical device wherein the one or more monomers are 2-ethyoxyethyl methacrylate and methyl methacrylate.

In an embodiment of the present invention, a durable controlled drug releasing polymeric coating is provided for an implantable medical device wherein the one or more monomers are 2-ethyoxyethyl methacrylate and hexyl methacrylate.

In another embodiment of the present invention, a durable controlled drug releasing polymeric coating is provided for an implantable medical device wherein the one or more monomers are 2-ethyoxyethyl methacrylate and butyl methacrylate.

In one embodiment of the durable controlled drug releasing polymeric coating for an implantable medical device of the present invention, the polymeric coating has a glass transition temperature (Tg) between about −9° C. and about 70° C.

In another embodiment of the durable controlled drug releasing polymeric coating for an implantable medical device of the present invention, the acrylate monomer has the structure of Formula 1;

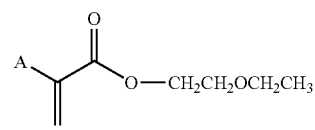

Formula 1 wherein A comprises methyl, ethyl, n-propyl, n-butyl, iso-butyl, sec-butyl, tert-butyl, linear or branched C5 to C18 moieties, cyclic C3 to C8 moieties, poly ethers, poly siloxanes and their heteroatomic derivatives.

In yet another embodiment of the durable controlled drug releasing polymeric coating for an implantable medical device of the present invention, the acrylate monomer has the structure of Formula 2;

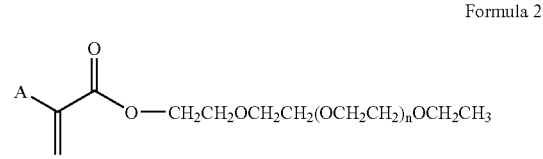

Formula 2 wherein n is an integer between about 0 and about 15,000, and A comprises methyl, ethyl, n-propyl, n-butyl, iso-butyl, sec-butyl, tert-butyl, linear or branched C5 to C18 moieties, cyclic C3 to C8 moieties, poly ethers, poly siloxanes and their heteroatomic derivatives.

In yet another embodiment of the durable controlled drug releasing polymeric coating for an implantable medical device of the present invention, the medical device is selected from the group consisting of vascular stents, shunts, vascular grafts, stent grafts, heart valves, catheters, pacemakers, pacemaker leads, bile duct stents and defibrillators.

In one embodiment of the durable controlled drug releasing polymeric coating for an implantable medical device of the present invention, the durable controlled drug releasing polymer coating is coated on an implantable medical device and the polymer-coated implantable medical device further comprises a drug.

In another embodiment of the durable controlled drug releasing polymeric coating for an implantable medical device of the present invention, the polymer-coated medical device releases the drug with a drug elution profile selected from the group consisting of a rapid large burst of drug followed by a steady release rate; a rapid small burst of drug followed by a steady release rate; and a gradual release of drug without a burst.

DEFINITION OF TERMS

Figure 1:
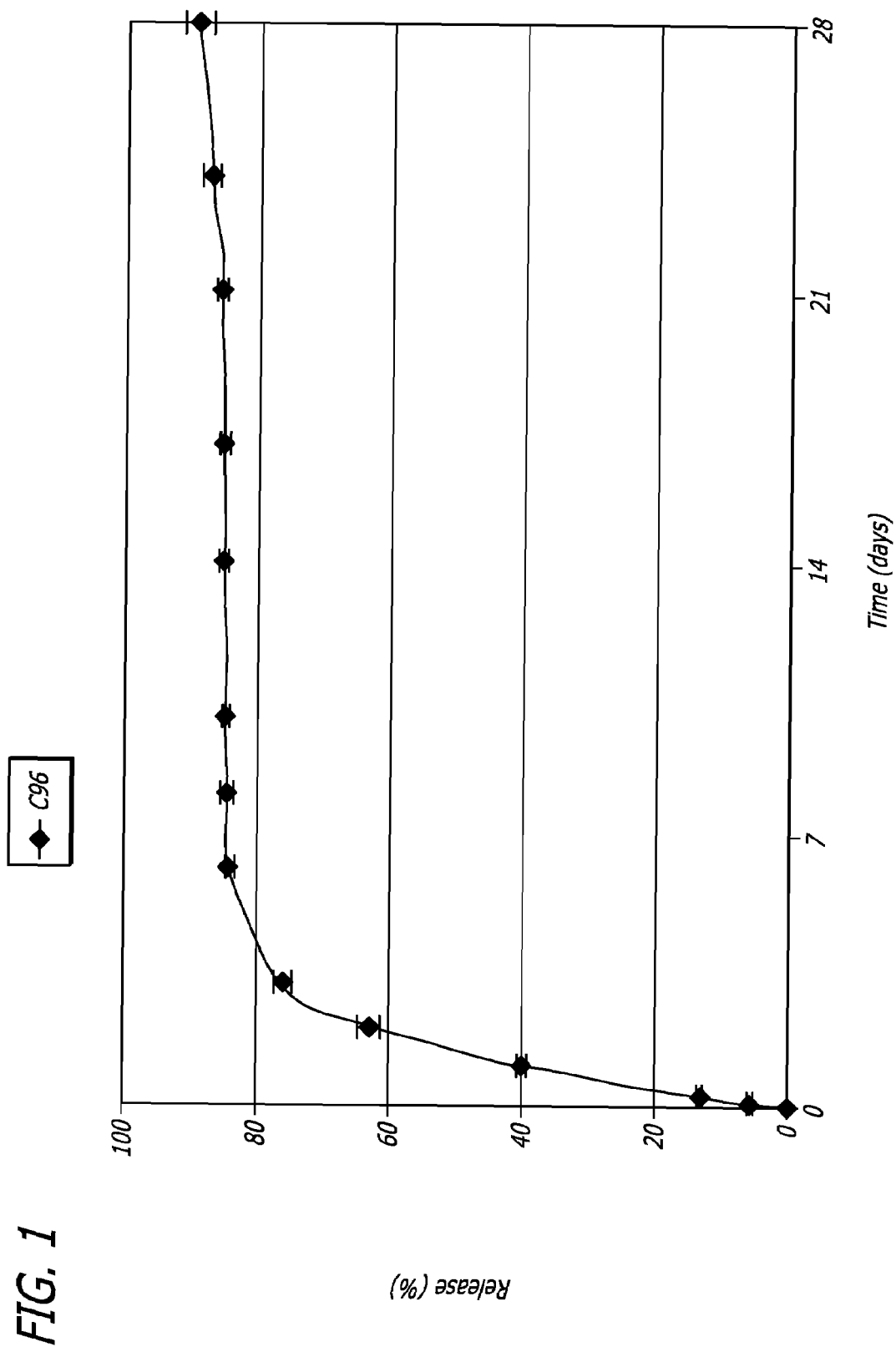
FIG. 1 graphically depicts a drug elution profile representing a rapid large burst of drug followed by a steady release rate from an exemplary polymer made according to the teachings of the present invention.

Prior to setting forth the invention, it may be helpful to an understanding thereof to set forth definitions of certain terms that will be used hereinafter:

Backbone: As used here in "backbone" refers to the main chain of a polymer or copolymer of the present invention. As used herein the backbone comprises acrylate based chains.

Biodegradable: As used herein "biodegradable" refers to a polymeric composition that is biocompatible and subject to being broken down in vivo through the action of normal biochemical pathways. From time-to-time bioresorbable and biodegradable may be used interchangeably, however, they are not coextensive. Biodegradable polymers may or may not be reabsorbed into surrounding tissues, however all bioresorbable polymers are considered biodegradable. The biodegradable polymers of the present invention are capable of being cleaved into biocompatible byproducts through chemical- or enzyme-catalyzed hydrolysis.

Copolymer: As used here in a "copolymer" will be defined as a macromolecule produced by the simultaneous or stepwise polymerization of two or more dissimilar units such as monomers. Copolymer shall include bipolymers (two dissimilar units), terpolymers (three dissimilar units), etc.

Compatible: As used herein "compatible" refers to a composition possing the optimum, or near optimum combination of physical, chemical, biological and drug release kinetic properties suitable for a controlled-release coating made in accordance with the teachings of the present invention. Physical characteristics include durability and elasticity/ductility, chemical characteristics include solubility and/or miscibility and biological characteristics include biocompatibility. The drug release kinetic should be either near zero-order or a combination of first and zero-order kinetics.

Controlled release: As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time.

Drug(s): As used herein "drug" shall include any bioactive agent having a therapeutic effect in an animal. Exemplary, non limiting examples include anti-proliferatives including, but not limited to, macrolide antibiotics including FKBP 12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Drugs can also refer to bioactive agents including anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

Ductility: As used herein "ductility, or ductile" is a polymer attribute characterized by the polymer's resistance to fracture or cracking when folded, stressed or strained at operating temperatures. When used in reference to the polymer coating compositions of the present invention the normal operating temperature for the coating will be between room temperature and body temperature or approximately between 15° C. and 40° C. Polymer durability in a defined environment is often a function of its elasticity/ductility.

Glass Transition Temperature (Tg): As used herein glass transition temperature (Tg) refers to a temperature wherein a polymer structurally transitions from a elastic pliable state to a rigid and brittle state.

Hydrophilic: As used herein in reference to the bioactive agent, the term "hydrophilic" refers to a bioactive agent that has a solubility in water of more than 200 micrograms per milliliter.

Hydrophobic: As used herein in reference to the bioactive agent the term "hydrophobic" refers to a bioactive agent that has a solubility in water of no more than 200 micrograms per milliliter.

Heteroatomic Derivatives: As used herein heteroatomic derivatives refers to molecules having two or more different atoms.

DETAILED DESCRIPTION OF THE INVENTION

Disclosed herein are durable controlled drug release polymers for coating and forming implantable medical devices. The polymers of the present invention form drug encapsulating matrices that enable controlled release of the drug. More specifically the drug release or eluting rates are controlled by, among other properties, glass transition temperature (Tg) of the polymer. The biocompatible controlled-release coatings described herein are durable, that is they do not delaminate from the medical device or suffer damage rendering the coating inoperable. The polymers of the present invention are biocompatible and bio-stable, that is they do not biodegrade. Additionally, the polymers of the present invention are not damaged by ethylene oxide sterilization.

Medical devices suitable for coating with the durable controlled drug releasing polymers of the present invention include, but are not limited to, vascular stents, stent grafts, urethral stents, bile duct stents, catheters, guide wires, pacemaker leads, bone screws, sutures and prosthetic heart valves. Medical devices which can be manufactured from the durable controlled drug releasing polymers of the present invention include, but are not limited to, vascular stents, stent grafts, urethral stents, bile duct stents, catheters, guide wires, pacemaker leads, bone screws, sutures and prosthetic heart valves.

The durable biocompatible controlled drug releasing polymers comprise a single monomer, or two or more monomers. In one embodiment of the present invention, the controlled drug releasing polymers comprise acrylic monomers. The acrylic monomers used in the present invention include, but are not limited to, methyl methacrylate, ethyl methacrylate, hexyl methacrylate, 2-ethoxyethyl methacrylate, lauryl methacrylate, hydroxy ethyl methacrylate and hydroxypropyl methacrylate. Additional monomers suitable for use in the polymers of the present invention include, but are not limited to, polyethylene glycol (PEG) acrylate esters. The polymers of the present invention comprise varying ratios of at least one monomer. By varying the amount of monomers used as well the reaction conditions the properties of the polymers can be fine tuned for drug delivery, more specifically controlled drug release rates. The polymers of the present invention are suitable for the controlled release of both hydrophobic and hydrophilic drugs, either independently or in combination. In one embodiment, the polymers of the present invention comprise 2-ethoxyethyl methacrylate.

The polymers of the present invention comprise both copolymers and single monomer polymers. The polymeric coatings of the present invention include copolymers, comprising at least two acrylic monomers. The monomers used in the present invention are not limited to acrylic based monomers. In one embodiment of the present invention the copolymer has a first polyethylene glycol (PEG) acrylate esters comprising 2-ethoxyethyl methacrylate and a second monomer comprising methyl methacrylate. In another copolymer of the present invention, the first monomer is 2-ethoxyethyl methacrylate and the second monomer is hexyl methacrylate. In yet another embodiment of the present invention, the first monomer is 2-ethoxyethyl methacrylate and the second monomer is butyl methacrylate. In yet another embodiment of the present invention, the first monomer is 2-ethoxyethyl methacrylate and the second monomer is ethyl methacrylate. In still another embodiment of the present invention, the first monomer is 2-ethoxyethyl methacrylate, the second monomer is hydroxypropyl methacrylate or hydroxyethyl methacrylate and the third monomer is any alkylmethacrylate with straight or branched alkyl, alkenyl, cyclic and heterocyclic groups comprising C1 to C18 wherein C1 to C18 refers to the monomer having between 1 and 18 carbon atoms. In one embodiment of the present invention the alkymethacrylate monomer comprises lauryl methacrylate.

In another embodiment of the present invention, polymers comprising hydrophilic monomers suitable for retaining and releasing hydrophilic drugs are provided. An exemplary hydrophilic monomer of the present invention is a polyethylene glycol acrylate ester. In one embodiment of the present invention, the PEG acrylate ester monomer has the structure of Formula 1 wherein A comprises methyl, ethyl, n-propyl, n-butyl, iso-butyl, sec-butyl, tert-butyl, linear or branched C5 to C18 moieties, cyclic C3 to C8 moieties, poly ethers, poly siloxanes and their heteroatomic derivatives. In another embodiment of the present invention, the PEG acrylate ester monomer has the structure of Formula 2, n is 0 or an integer greater than 1 and A comprises methyl, ethyl, n-propyl, n-butyl, iso-butyl, sec-butyl, tert-butyl, linear or branched C5 to C18 moieties, cyclic C3 to C8 moieties, poly ethers, poly siloxanes and their heteroatomic derivatives. A PEG acrylate ester as described in the present invention comprises an alkyl capped PEG unit that is esterified with an acrylate monomer. An ester as used herein is the chemical functional group comprising oxygen bonded to the carbon of a carbonyl group.

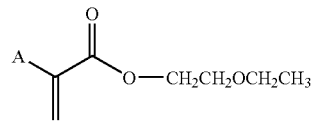

Formula 1

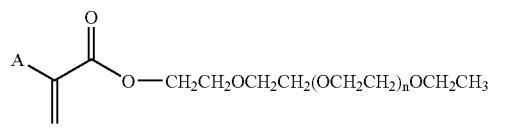

Formula 2

The synthesis of non-commercially available PEG acrylate ester monomers, having polyethylene glycol units larger than 1, in the present invention includes esterification reactions of various acrylic acids. Monomers of Formula 2 are synthesized from the appropriate methyl-capped polyethylene glycol (MPEG) units. The MPEGs of differing lengths (different n) are available from commercial sources (Sigma-Aldrich Chemical Co., St. Louis, Mo.). Esterification of the alkylacrylic acids in the presence of alcohols such as MPEGs is widely known to those of ordinary skill in the art. A non-limiting example of a procedure for esterification follows. The alkyl capped PEG is dissolved in tetrahydrofuran along with an acrylic acid. Sulfuric acid is added to the reaction mixture. Once the reaction is complete, the monomers are isolated according to standard procedures. The process involves acid catalyzed dehydration of the reaction mixture to allow for esterification to proceed. The synthetic methodology discussed permits full control over monomer selection and affords the practitioner a broad range of monomers.

Controlling drug release rates from the polymers of the present invention requires adjusting the properties of the polymers including monomer selection. One non-limiting method of controlling drug release rates in the polymers of the present invention involves controlling the Tgs of the polymers. Lower Tgs, e.g. −10° C., in drug eluting polymers, without being held to the theory, result in faster elution of drugs from the polymers while higher Tgs have slower drug eluting profiles. Incorporating acrylic monomers that have shorter alkyl chains bonded to them will raise the Tg whereas lower ratios of acrylic monomers that have shorter alkyl chains bonded to them will depress the Tg.

Both copolymers and homopolymers of the present invention are adjusted for varying Tgs. The methods for controlling Tgs include varying monomer ratios in copolymers, employment of appropriate monomers for homopolymers, controlling reaction conditions and controlling post-synthetic manipulations of the polymer. Varying the monomer ratios of the copolymers having at least two different monomers enables control over Tgs. In one embodiment of the present invention, the increase in butyl methacrylate monomer ratios with respect to 2-ethoxyethyl methacrylate monomers produces copolymers with higher Tgs. In contrast, as the ratio of butyl methacrylate decreases with respect to 2-ethoxyethyl methacrylate, the Tgs of the resulting polymers decrease.

In one embodiment, the polymers of the present invention can be used to form and coat medical devices. Coating polymers having relatively high Tgs can result in medical devices with unsuitable drug eluting properties as well as unwanted brittleness. In the cases of polymer-coated vascular stents, a relatively low Tg in the coating polymer effects the deployment of the vascular stent. For example, polymer coatings with low Tgs are "sticky" and adhere to the balloon used to expand the vascular stent during deployment, causing problems with the deployment of the stent. Low Tg polymers, however, have beneficial features in that polymers having low Tgs are more elastic at a given temperature than polymers having higher Tgs. Expanding and contracting a polymer-coated vascular stent mechanically stresses the coating. If the coating is too brittle, i.e. has a relatively high Tg, then fractures may result in the coating possibly rendering the coating inoperable. If the coating is elastic, i.e has a relatively low Tg, then the stresses experienced by the coating are less likely to mechanically alter the structural integrity of the coating. Therefore, the Tgs of the polymers of the present invention can be fine tuned for appropriate coating applications by a combination of monomer composition and synthesis conditions. The polymers of the present invention are engineered to have adjustable physical properties enabling the practitioner to choose the appropriate polymer for the function desired.

The present invention also takes into account fine tuning, or modifying, the glass transition temperature (Tg) of the durable biocompatible controlled drug release polymers. Drug elution from polymers depends on many factors including density, the drug to be eluted, molecular composition of the polymer and Tg. Higher Tgs, for example temperatures above 40° C., result in more brittle polymers while lower Tgs, e.g. lower than 40° C., result in more pliable and elastic polymers at higher temperatures. Drug elution is slow from polymers that have high Tgs while faster rates of drug elution are observed with polymers possessing low Tgs. In one embodiment of the present invention, the Tg of the polymer is selected to be lower than 37° C.

Various methods are employed to coat the medical devices. In one embodiment of the present invention the polymers are dissolved in a volatile solvent along with a drug and sprayed onto the medical device. In another embodiment of the present invention the medical device is dipped in a solution containing the polymer and the drug. The volatile solvent is then allowed to evaporate and the coated medical device is presented. The coating polymers of the present invention do not delaminate from the medical devices, they are durable.

The controlled release polymeric coatings of the present invention can be applied to medical device surfaces, either primed or bare, in any manner known to those skilled in the art. Applications methods compatible with the present invention include, but are not limited to, spraying, dipping, brushing, vacuum-deposition, and others. Moreover, the controlled-release coatings of the present invention may be used with a cap coat. A cap coat as used here refers to the outermost coating layer applied over another coating. A drug-releasing copolymer coating is applied over the primer coat. A polymer cap coat is applied over the drug-releasing copolymer coating. The cap coat may optionally serve as a diffusion barrier to further control the drug release, or provide a separate drug. The cap coat may be merely a biocompatible polymer applied to the surface of the sent to protect the stent and have no effect on elution rates. One aspect of the present invention is to provide a biodegradable cap coat that protects the device and bioactive agent from the environment until implanted. After implantation is complete, the biodegradable cap coat degrades at a predetermined rate (made possible by the additional and modification of functional groups to the polymer backbone as made in accordance with the teachings of the present invention) exposing the medical device surface and bioactive agent to the physiological environment.

The methods described are also useful for coating medical devices only a portion of the medical device such that the medical device contains portions that provide the beneficial effects of the coating and portions that are uncoated. The coating steps can be repeated or the methods combined to provide a plurality of layers of the same coating or a different coating. In one embodiment, each layer of coating comprises a different polymer or the same polymer. In another embodiment each layer comprises the same drug or a different drug.

Figure 2:
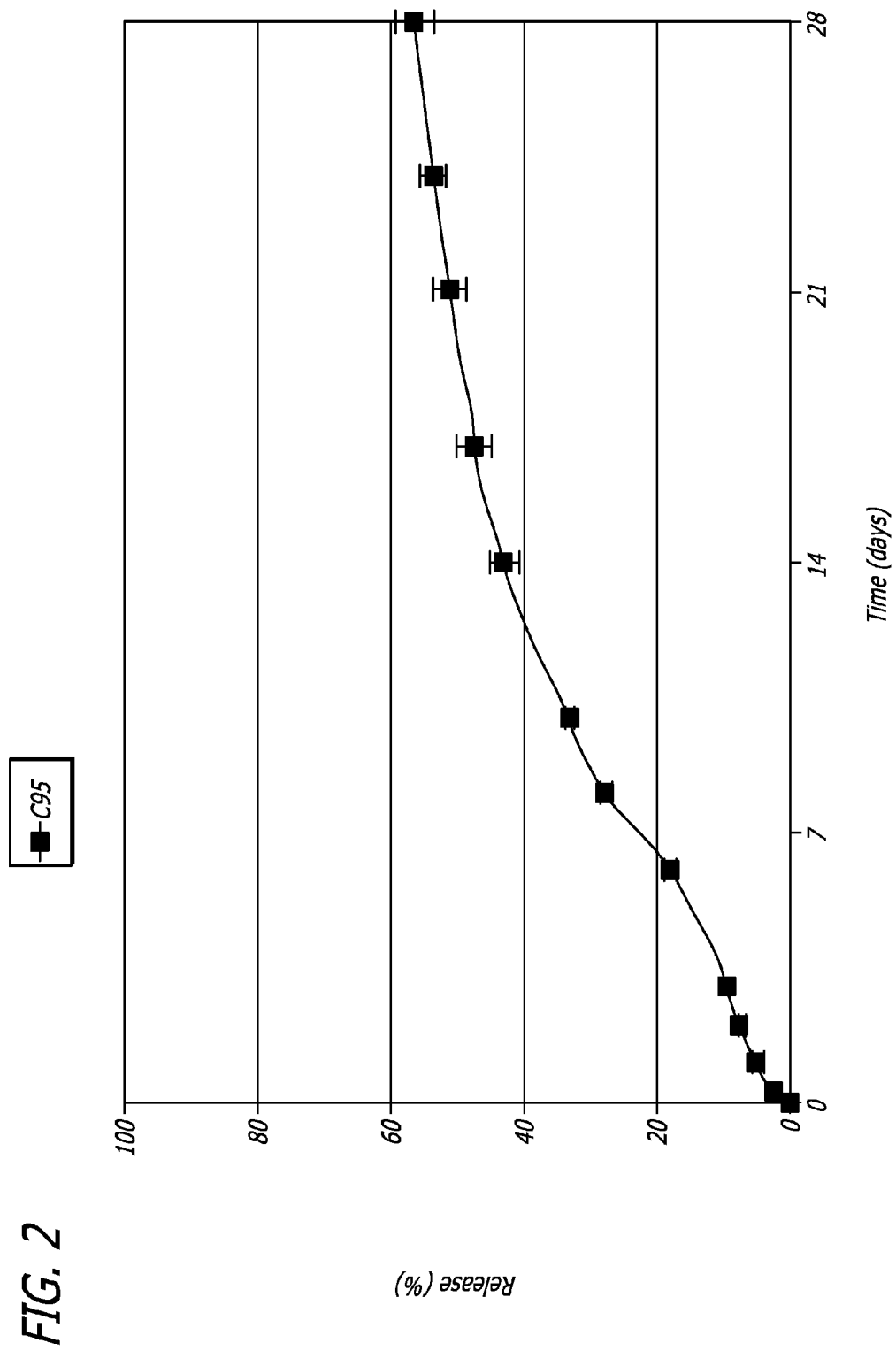
FIG. 2 graphically depicts a drug elution profile representing a rapid small burst of drug followed by a steady release rate from an exemplary polymer made according to the teachings of the present invention.
Figure 3:
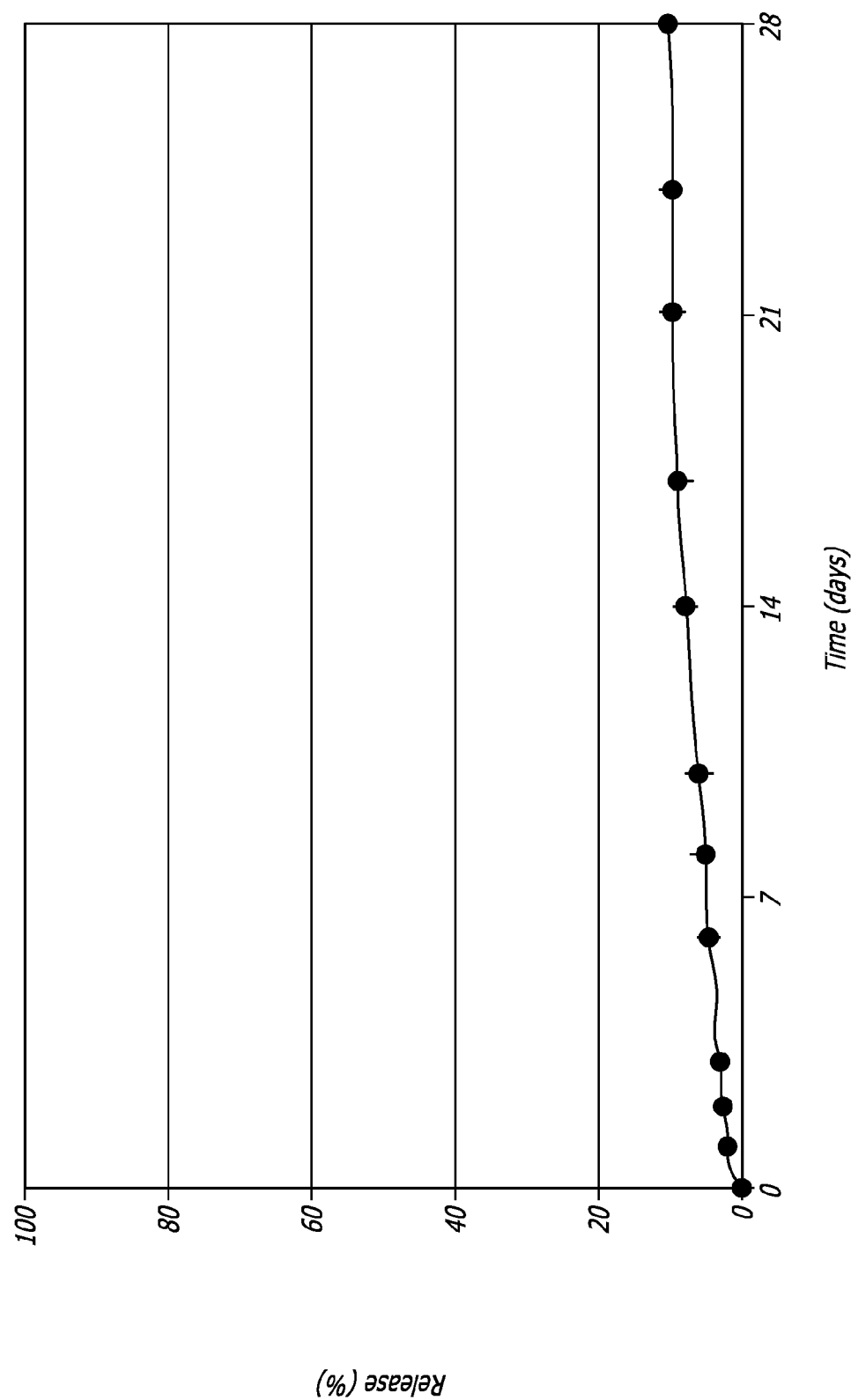
FIG. 3 graphically depicts a drug elution profile representing a gradual release of drug from an exemplary polymer made according to the teachings of the present invention.

In the present invention controlled drug eluting biocompatible polymers for coating medical devices are presented. Depending on the polymer, various rates of drug elution are available in the present invention. In one embodiment of the present invention a rapid large burst is observed in the drug elution profile followed by a steady release rate of the drug (FIG. 1). In another embodiment of the present invention a gradual drug release rate is observed without an initial burst (FIG. 3). In yet another embodiment of the present invention a rapid small burst is observed followed by a steady release rate of the drug (FIG. 2).

Various classes of drugs are eluted with the polymers of the present invention including, but not limited to, anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like. An exemplary drug suitable for eluting from the polymers of the present invention is rapamycin. Rapamycin inhibits the proliferation of vascular smooth muscle cells and thereby prohibits restenosis of an artery after implantation of a vascular stent.

The present invention also includes implantable medical devices and coatings for medical devices made from one or more of the polymers of the present invention. Moreover, the medical devices and coating made in accordance with the teachings of the present invention include controlled-release coatings wherein one or more bioactive agent is eluted from the polymer in a predetermined fashion. Exemplary embodiments include, but are not limited to, drug-eluting vascular stents and coatings therefore wherein anti-proliferative bioactive agents are released in situ such that restenosis is treated, prevented or inhibited. Suitable bioactive agents include, but are not limited to, FKBP 12 binding compounds such as zotarolimus, estrogens, chaperone inhibitors, protease inhibitors, protein-tyrosine kinase inhibitors, leptomycin B, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids.

EXAMPLES

Example 1

The synthesis of a monomer having Formula 2 where A is H and n is about 350 is described.

To a solution of acrylic acid (72 g, 1 mol) in tetrahydrofuran (200 mL) is added a 500 mL MPEG (n about 350) solution (in water, d=1.088 g/ml). Then p-tolusulfonic acid (1g, 0.005 mol) is added to the mixture and the esterification reaction started under vacuum (about 30 torr). Once the reaction is completed the monomers are harvested by evaporating the tetrahydrofuran.

Example 2

The synthesis of a copolymer comprising the monomers 2-ethoxyethyl methacrylate and hexyl methacrylate is described.

To a solution of 2-ethoxyethyl methacrylate (10 g, 0.06 mol) in 2-butanone (14 mL) and n-propyl alcohol (6 mL) is added hexyl methacrylate (10.08 g, 0.06 mol) and the initiator azobisisobutyronitrile (160 mg). The reaction mixture is stirred for 5 hours at 60° C. Once the reaction is completed the polymer is precipitated in cold methanol (−60° C.) and re-dissolved in chloroform. This purification is repeated three times. The final purified polymer is harvested by evaporating the solvents.

Example 3

The coating of a vascular stent with drug impregnated polymers is described.

To a solution of coating polymer, for example, the polymer of Example 2, and rapamycin in tetrahydrofuran is added a vascular stent. The vascular stent is removed and allowed to dry, the solvent evaporated. A drug eluting stent is presented. The controlled release polymeric coatings of the present invention can be applied to medical device surfaces, either primed or bare, in any manner known to those skilled in the art. Applications methods compatible with the present invention include, but are not limited to, spraying, dipping, brushing, vacuum-deposition, and others. Moreover, the controlled-release coatings of the present invention may be used with a cap coat. A cap coat as used here refers to the outermost coating layer applied over another coating. A drug-releasing copolymer coating is applied over the primer coat. A polymer cap coat is applied over the drug-releasing copolymer coating. The cap coat may optionally serve as a diffusion barrier to further control the drug release, or provide a separate drug. The cap coat may be merely a biocompatible polymer applied to the surface of the sent to protect the stent and have no effect on elution rates. One aspect of the present invention is provide a biodegradable cap coat that protects the device and bioactive agent from the environment until implanted. After implantation is complete, the biodegradable cap coat degrades at a predetermined rate (made possible by the additional and modification of functional groups to the polymer backbone as made in accordance with the teachings of the present invention) exposing the medical device surface and bioactive agent to the physiological environment.

The methods described are also useful for coating medical devices only a portion of the medical device such that the medical device contains portions that provide the beneficial effects of the coating and portions that are uncoated. The coating steps can be repeated or the methods combined to provide a plurality of layers of the same coating or a different coating. In one embodiment, each layer of coating comprises a different polymer or the same polymer. In another embodiment each layer comprises the same drug or a different drug.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A durable controlled drug releasing polymeric coating for an implantable medical device comprising:
   a first monomer and optionally a second monomer wherein said first monomer is 2-ethoxyethyl methacrylate and said second monomer is an acrylate monomer; and
   a drug,
   wherein said durable controlled drug releasing polymeric coating comprises a drug elution profile selected from the group consisting of a rapid large burst of drug followed by a steady release rate; a rapid small burst of drug followed by a steady release rate; and a gradual release of drug without a burst.

2. The durable controlled drug releasing polymeric coating for an implantable medical device of claim 1 wherein said second monomer is an acrylate monomer selected from the group consisting of hexyl methacrylate, butyl methacrylate, ethyl methacrylate, lauryl methacrylate, hydroxyl propylmethacrylate and hydroxyl ethylmethacrylate.

3. The durable controlled drug releasing polymeric coating for an implantable medical device of claim 2 wherein said second monomer is methyl methacrylate.

4. The durable controlled drug releasing polymeric coating for an implantable medical device of claim 2 wherein said second monomer is hexyl methacrylate.

5. The durable controlled drug releasing polymeric coating for an implantable medical device of claim 2 wherein said second monomer is butyl methacrylate.

6. The durable controlled drug releasing polymeric coating for an implantable medical device of claim 2 wherein said second monomer is ethyl methacrylate.

7. The durable controlled drug releasing polymeric coating for an implantable medical device of claim 2 further comprising a third monomer, wherein said second monomer is hydroxyl ethylmethacrylate or hydroxyl propylmethacrylate and said third monomer is an alkylmethacrylate.

8. The durable controlled drug releasing polymeric coating for an implantable medical device of claim 7 wherein said alkylmethacrylate comprises straight or branched alkyl, alkenyl, cyclic and heterocyclic groups comprising C1 to C18.

9. The durable controlled drug releasing polymeric coating for an implantable medical device of claim 8 wherein said alkylmethacrylate is lauryl methacrylate.

10. The durable controlled drug releasing polymeric coating for an implantable medical device of claim 1 wherein said polymeric coating has a glass transition temperature (Tg) between about −9° C. and about 70° C.

11. The durable controlled drug releasing polymeric coating for an implantable medical device of claim 1 wherein said acrylate monomer has the structure of Formula 1;

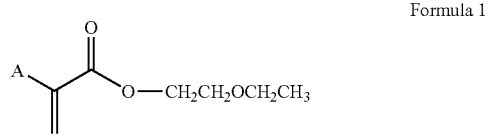

Formula 1 wherein A comprises methyl, ethyl, n-propyl, n-butyl, isobutyl, sec-butyl, tert-butyl, linear or branched C5 to C18 moieties, cyclic C3 to C8 moieties, poly ethers, poly siloxanes and their heteroatomic derivatives.

12. The durable controlled drug releasing polymeric coating for an implantable medical device of claim 1 wherein said acrylate monomer has the structure of Formula 2;

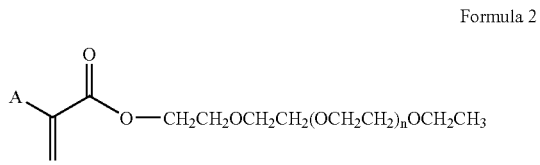

Formula 2 wherein n is an integer between about 0 and about 15,000, and A comprises methyl, ethyl, n-propyl, n-butyl, isobutyl, sec-butyl, tert-butyl, linear or branched C5 to C18 moieties, cyclic C3 to C8 moieties, poly ethers, poly siloxanes and their heteroatomic derivatives.

13. The durable controlled drug releasing polymeric coating for an implantable medical device of claim 1 wherein said medical device is selected from the group consisting of vascular stents, shunts, vascular grafts, stent grafts, heart valves, catheters, pacemakers, pacemaker leads, bile duct stents and defibrillators.

14. The durable controlled drug releasing polymeric coating for an implantable medical device of claim 1 wherein said durable controlled drug releasing polymer coating is coated on an implantable medical device.

* * * * *